US007312869B2

(12) United States Patent
Wang

(10) Patent No.: US 7,312,869 B2
(45) Date of Patent: Dec. 25, 2007

(54) OUT-OF-PLANE BIREFRINGENCE MEASUREMENT

(75) Inventor: Baoliang Wang, Beaverton, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 371 days.

(21) Appl. No.: 11/155,825

(22) Filed: Jun. 16, 2005

(65) Prior Publication Data

US 2005/0219528 A1    Oct. 6, 2005

Related U.S. Application Data

(63) Continuation of application No. PCT/US03/040366, filed on Dec. 19, 2003.
(60) Provisional application No. 60/492,838, filed on Aug. 6, 2003, provisional application No. 60/435,588, filed on Dec. 20, 2002.

(51) Int. Cl.
*G01J 4/00* (2006.01)

(52) U.S. Cl. .................................................. 356/365
(58) Field of Classification Search ................. 356/365
See application file for complete search history.

(56) References Cited

U.S. PATENT DOCUMENTS 5,956,146 A * 9/1999 Nakagawa ................... 356/365

* cited by examiner

*Primary Examiner*—Roy M. Punnoose
(74) *Attorney, Agent, or Firm*—Hancock Hughey LLP

(57) ABSTRACT

The disclosure is directed to precise measurement of out-of-plane birefringence properties of samples of transparent optical material. Two angled-apart light beams are passed through a selected location of a sample optical element. One of the beams is incident to the sample surface. The characteristics of the beams are detected after passing through the sample, and the information detected is processed to determine the out-of-plane birefringence.

30 Claims, 5 Drawing Sheets

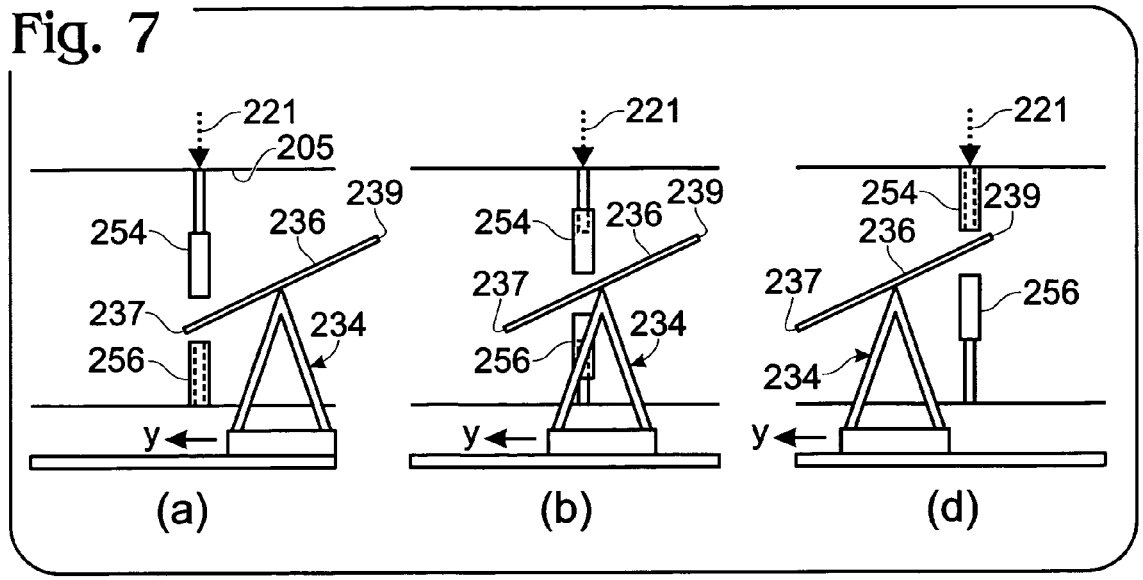
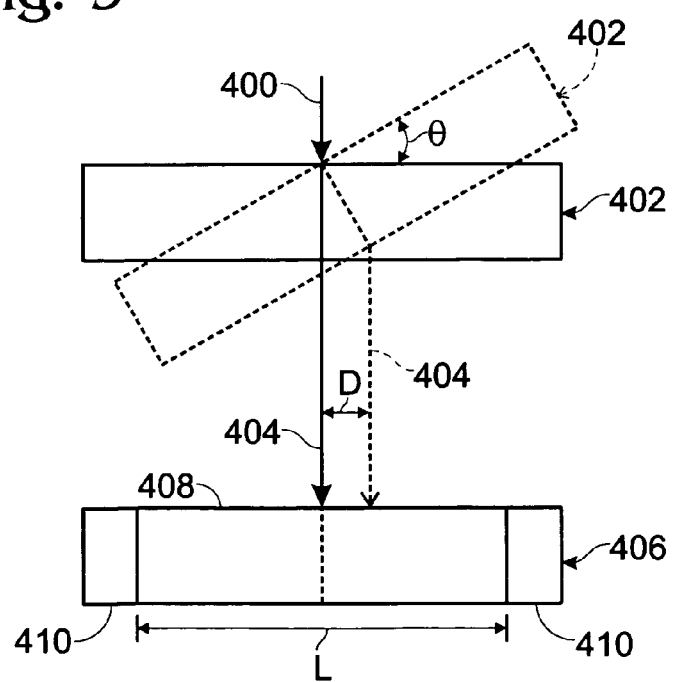

OUT-OF-PLANE BIREFRINGENCE MEASUREMENT

TECHNICAL FIELD

This application relates to measurement of birefringence properties of optical material, and primarily to the measurement of out-of-plane birefringence of such material.

BACKGROUND

Many important optical materials exhibit birefringence. Birefringence causes different linear polarizations of light to travel at different speeds through the material. These different polarizations are most often considered as two components of the polarized light, one component being orthogonal to the other.

Birefringence is an intrinsic property of many optical materials, and may also be induced by external forces applied to the material. The induced birefringence may be temporary, as when the material is oscillated, or the birefringence may be residual, as may happen when, for example, the material undergoes thermal stress during production of the material.

Retardation or retardance represents the integrated effect of birefringence acting along the path of a light beam that traverses a sample of the optical material. If the incident light beam is linearly polarized, the two orthogonal components of the polarized light will exit the sample with a phase difference, called the retardance. The fundamental unit of retardance is length, such as nanometers (nm). It is frequently convenient, however, to express retardance in units of phase angle (waves, radians, or degrees), which is proportional to the retardance (nm) divided by the wavelength of the light (nm). An "average" birefringence for a sample is sometimes computed by dividing the measured retardation magnitude by the thickness of the sample.

The two orthogonal, polarized beam components mentioned above are parallel to two orthogonal axes associated with the optical material, which axes are referred to as the "fast axis" and the "slow axis." The fast axis is the axis of the material that aligns with the faster moving component of the polarized light through the sample. Therefore, a complete description of the retardance of a sample along a given optical path requires specifying both the magnitude of the retardance and the relative angular orientation of the fast (or slow) axis of the sample.

The need for precise measurement of birefringence properties has become increasingly important in a number of technical applications. For instance, it is important to specify linear birefringence in optical elements that are used in high-precision instruments employed in semiconductor and other industries.

The prior art, including U.S. Pat. No. 6,473,747, Birefringence Measurement System, hereby incorporated by reference, discloses methods and apparatus for measuring birefringence of a sample using a light beam that is directed through the sample at a normal (zero-degree) incidence angle relative to the surface of the sample. As a result, the determination of the sample's birefringence is "in-plane," meaning that the determination essentially represents the difference between the indices of refraction of two orthogonal axes in a plane of the sample, that plane being normal to the incident light beam.

The effect of birefringence on displayed visible light (such effects occurring, for example, when the light passes through an optical film or coating) may be to reduce contrast or alter colors. Also, with many materials, such as those used with liquid crystal display (LCD) panels, the extent or magnitude of birefringence is a function of the incident angle of the light under consideration. For example, increasing (from normal) the viewing angle of a LCD panel will increase the birefringence effect on the light emanating from the panel and, without compensation, reduce the perceived quality of the visible light by reducing contrast and/or altering colors.

Transparent polymer films have been developed for use with LCD panels for the purpose of compensating for the just-noted birefringence variations attributable to viewing angle. In short, these films possess birefringence characteristics that compensate for the birefringence of the LCD panel and thus provide a wide viewing angle without significant loss of contrast or color.

It is important to properly characterize the birefringence of such films, and other optical materials, in planes that are parallel to the normal (zero-degree) angle of incidence. This birefringence measure can be referred to as "vertical" or "out-of-plane" birefringence. One can consider the notion of in-plane and out-of-plane birefringence in terms of a Cartesian coordinate system. Accordingly, if the normal-incidence light is considered to travel in a direction parallel to the Z-axis of such a coordinate system, the in-plane birefringence occurs in the XY plane of the sample. Out-of-plane birefringence is in a plane perpendicular to the in-plane birefringence, thus occurring in the XZ or YZ plane.

Other applications (in additional to the birefringence compensation film example just discussed) may call for precise determination of out-of-plane birefringence. For example, certain cubic crystals, such as calcium fluoride, may exhibit intrinsic birefringence when short-wavelength light (for example, 157 nm) propagates through the crystal. The intrinsic birefringence is greatest between the [001] and [110] axes of the crystal. Also, such crystals are often produced with an outer surface or "window" for receiving incident light normal to the [111] surfaces of the crystal. As a result, the just mentioned intrinsic birefringence present between the [001] and [110] axes of the crystal is out-of-plane birefringence relative to the light that is normal to the [111] surface. The difference with the Cartesian corrdinate anoalogy mentioned in the prior paragraph is that the [111] axis is not normal to the [110] or [001] axes. Nevertheless, it is still amenable to the measurement techniques of the present invention as summarized next.

SUMMARY OF THE INVENTION

The present invention is directed to precise measurement of out-of-plane birefringence properties of samples of transparent optical material.

In one preferred embodiment, two angled-apart light beams are passed through a selected location of a sample. One of the beams is directed to be normally incident to the sample surface. The characteristics of the beams are detected after passing through the sample, and the information obtained is processed to determine the out-of-plane birefringence.

Other advantages and features of the present invention will become clear upon study of the following portion of this specification and the drawings.

BRIEF DESCRIPTION OF THE DRAWINGS

FIG. 7 is a three-part diagram showing an embodiment wherein a sample optical element that is held in an inclined or tilted orientation is moved relative to the beam path.

FIG. 9 is a diagram showing the tilting of an optical element and the related effect on the light beam path through the sample.

DETAILED DESCRIPTION

In accordance with the present invention, the out-of-plane birefringence occurring at a location in a sample is determined by passing two angled-apart light beams through that location. One of the beams is directed to be normal to the surface of the sample. Thus, upon exiting the sample, that light beam provides information relating to the in-plane birefringence of the sample.

The other light beam is directed to be oblique to the sample surface and thus exits the sample with characteristics that provide information relating to the retardance occurring along the (refracted) incident path of the second beam through the sample. The information provided by the two angled-apart beams is detected and processed to provide, in addition to the in-plane birefringence of the sample, the out-of-plane birefringence of the sample, as will be described more fully below.

Figure 1:
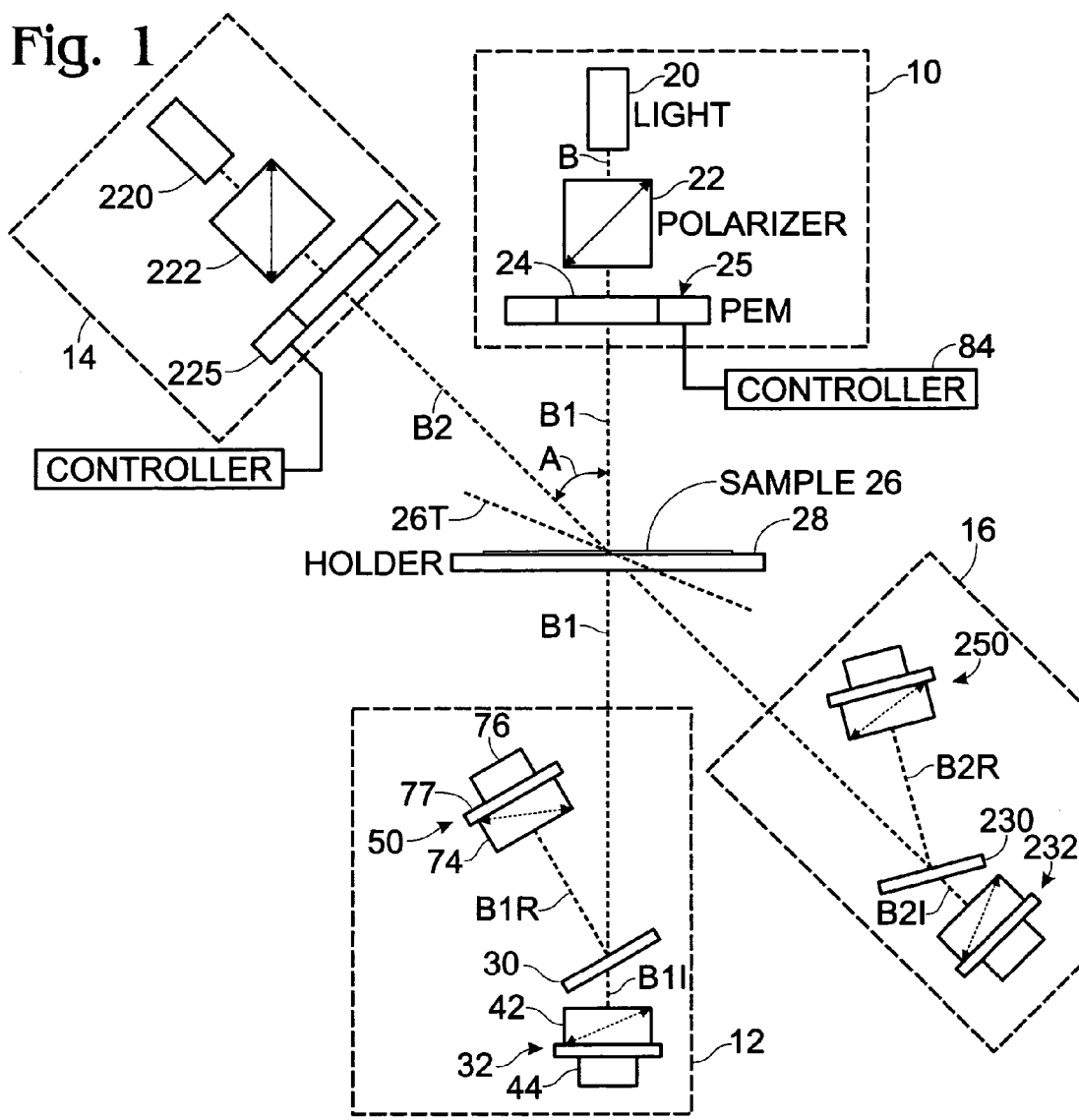
FIG. 1 is a diagram of one embodiment showing a preferred arrangement of the optical components of a system that is used for measuring out-of-plane birefringence in accordance with the present invention.
Figure 2:
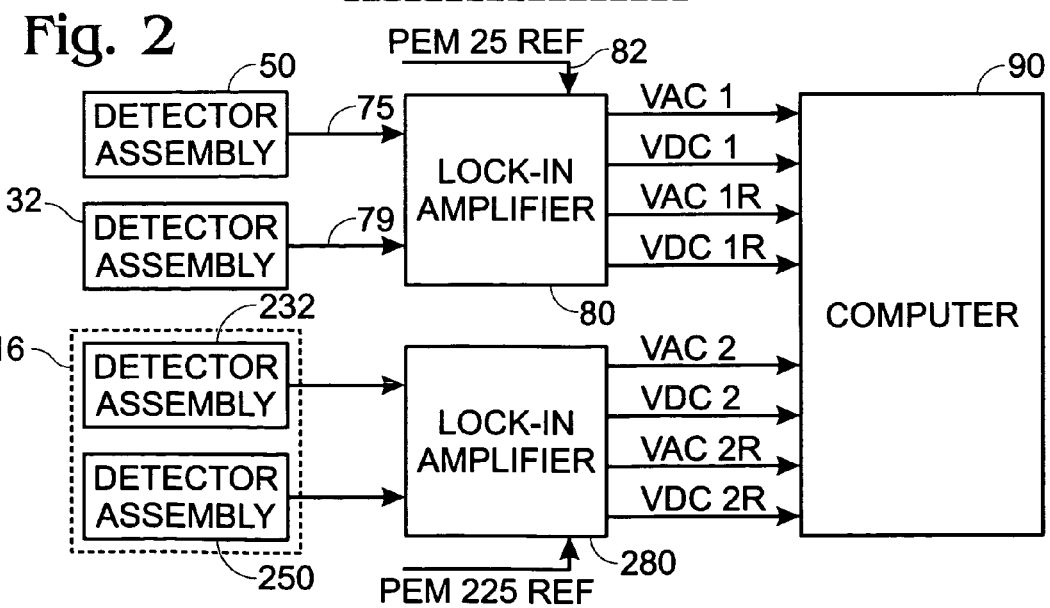
FIG. 2 is a block diagram of the signal processing components of the system depicted in FIG. 1.

One embodiment of a system for measuring out-of-plane birefringence is described with reference to FIGS. 1 and 2. The diagram of FIG. 1 depicts the primary optical components of the system. The components can be grouped and discussed as modules. The embodiment of FIG. 1 depicts a normal source module 10, a normal detection module 12, an oblique source module 14, and an oblique detection module 16. The terms "normal" and "oblique" are used as adjectives here to respectively distinguish modules associated with a light beam directed through the sample at a normal or zero-angle incidence from modules associated with a beam directed through the sample at an oblique angle, as explained more fully below.

The components of the normal source module 10 include a HeNe laser as a light source 20. That laser has a wavelength of 632.8 nanometers (nm). It is contemplated that the wavelength of the source light can be selected to best match the particular application.

The beam "B" emanating from the source 20 has a cross sectional area or "spot size" of approximately 1.0 millimeter (mm). The source light beam is directed to be incident upon a polarizer 22 that is oriented with its polarization direction at +45° relative to a baseline axis. A high-extinction polarizer, such as a Glan-Thompson calcite polarizer, is preferred. It is also preferred that the polarizer 22 be secured in a precision, graduated rotator.

The polarized light emanating from the polarizer 22 is incident upon the optical element 24 of a photoelastic modulator 25. In a preferred embodiment, the photoelastic modulator (hereafter referred to as a "PEM") is one manufactured by Hinds Instruments, Inc., of Hillsboro, Oreg. It is noteworthy here that although a PEM is preferred, other mechanisms could be used for modulating the polarization of the source light.

Most accurate retardance measurements are achieved when one minimizes the residual birefringence present in the optical components of the system. To this end, the PEM 25 should be configured to eliminate residual birefringence that may be otherwise produced by the forces present in supporting the optical element 24 of the PEM.

The PEM 25 has its birefringent axis oriented at 0° and is controlled by a controller 84 that imparts an oscillating birefringence to the optical element 24, preferably at a nominal frequency of 50 kHz. In this regard, the controller drives two quartz transducers between which the optical element 24 is adhered.

The oscillating birefringence of the PEM 25 introduces a time-varying phase difference between the orthogonal components of the polarized light that propagates through the PEM. At any instant in time, the phase difference represents the retardation introduced by the PEM. As noted earlier, the retardation is measurable in units of length, such as nanometers. The PEM is adjustable to allow variation of the amplitude of the retardation introduced by the PEM. In the case at hand, the retardation amplitude is selected to be 0.383 waves (242.4 nm).

The beam of light "B1" propagating from the PEM 25 is directed through a transparent sample 26. The sample is supported in the path of the beam by a sample holder 28 that is controllable for periodically moving the sample in a translational sense along orthogonal (X and Y) axes (here considering light beam "B1" to be traveling in the Z axis).

Inasmuch as the sample 26 may be, for example, a thin, flexible polymeric film, a preferred holder would be one that comprises a plurality of spaced-apart, small-diameter (for example 1 or 2 mm) wires tightly strung between two rigid support members. The wires could be stainless steel wire rope that may or may not be coated with a low-friction coating. Nylon-coated wire rope and a number of other materials may also be used for the wires. The wire material, the tension applied to the wire, and the spacing between each wire is selected so that, depending on the weight of the sample, the sample is held in a plane without any bending stress, which might be introduced if the sample were permitted to sag. The spacing between individual wires in the holder 28 is as large as possible (depending upon the unit weight and flexibility of the sample 26) so that, as just mentioned, the space occupied by the wires underlying the sample is minimized.

The sample holder 28 may be driven by a conventional X-Y stage mechanism to translate the sample as mentioned above and thereby enable scanning of the sample 26 with the beam "B1" at a plurality of locations across the area of the sample.

The beam "B1" is affected by the in-plane birefringence of the sample 26 as the beam passes through the sample. The affect, as discussed above is to produce retardance in the beam. The in-plane birefringence that produces this retardance is determined in accordance with the present invention, as explained more below, and is also used for determining out-of-plane birefringence.

In order to obtain an unambiguous measure of the sample-induced, in-plane retardance, the beam "B1" that passes out of the sample 26 is separated into two parts having different polarization directions and thereby defining two channels of information for subsequent processing.

A preferred mechanism for separating the beam "B1," includes a beam-splitting mirror 30 that is a component of the normal detection module 12 and is located in the path of that beam (hereafter referred to as the incidence path). The beam-splitting mirror 30 is preferably made of Schott Glass type SF-57 glass. This glass has an extremely low (near zero) stress-optic coefficient. It is noteworthy here that, although a beam-splitting mirror is preferred, one can substitute other mechanisms (such as a flipper mirror arrangement) for separating the beam "B1" into two parts.

Beam "B1" passes completely through the beam-splitting mirror 30 and, now designated "B1I," enters a detector assembly 32 for detection. The detector assembly 32 includes a compact, Glan-Taylor type analyzer 42 that is arranged such that its polarization direction is at −45° from the baseline axis. From the analyzer 42, the beam "B1I" enters a detector 44, which is described more below.

The reflective surface of the beam-splitting mirror 30 faces upwardly, generally toward the sample 26. The mirror is mounted so that the incidence path (that is, the optical path of the beam "B1" as it propagates from the sample 26) is nearly normal to the reflective surface of the mirror. In a preferred embodiment, the angle made between the beam "B1" traveling along the incidence path and the beam part "B1R" that is reflected from the mirror 30 is greater than 0° but less than 10°.

The reflected part of the beam "B1R" is incident upon another detector assembly 50. That assembly 50 is configured and arranged to be adjacent to the incident beam "B1" and located to receive the reflected beam "B1R." The components of detector 50 are compactly integrated and housed to include a Glan-Taylor type analyzer 74 that is arranged so that its polarization direction is 0°, parallel with the birefringence axis of the PEM 25.

Stacked above the analyzer 74 is a narrow-band interference filter 77 that permits passage of polarized laser light but blocks unwanted room light from reaching a detector 76. The detector is preferably a photodiode that is stacked above the filter. The photodiode detector 76 is the preferred detection mechanism and produces as output a current signal representative of the time varying intensity of the received laser light. With respect to this detector assembly 50, the detected laser light is that of the beam "B1R," which is the reflected part of the beam that propagated through the sample 26.

The photodiode output of the detector assembly 50 is delivered to a preamplifier that is carried on an associated printed circuit board (not shown) that is part of the detector assembly 50. The preamplifier provides output 75 (FIG. 2) to a phase sensitive device (preferably a lock-in amplifier 80, or comparable computer-based digital signal processing components) in the form of a low-impedance intensity signal VAC1R, and a DC intensity signal VDC1R, which represents the time average of the detector signal.

The other detector assembly 32 (FIG. 1) mentioned above and to which is directed the non-reflected part "B1I" of the beam "B1" is, except in two respects, the same construction as the just described assembly 50. The detector assembly 32 is arranged so that the polarization direction of analyzer 42 is oblique to the polarization direction of the analyzer 74 in the other detector assembly 50. Specifically, the analyzer 42 is positioned with its polarization direction at −45°. Also, the photodiode of detector assembly 32 produces as output a current signal representative of the time varying intensity of the received laser light, which is the non-reflected part "B1I" of the beam "B1" that propagated through the sample 26.

The photodiode output of the detector assembly 32 is delivered to a preamplifier, which provides its output 79 to the lock-in amplifier 80 (FIG. 2) in the form of a low-impedance intensity signal VAC1, and a DC intensity signal VDC1, which represents the time average of the detector signal.

In summary, the lock-in amplifier 80 is provided with two channels of input. One channel corresponds to the output of detector assembly 32, and the other channel corresponds to the output of detector assembly 50. The intensity information received by the lock-in amplifier via the first channel—because of the arrangement of the −45° analyzer 42—relates to the 0° or 90° component of the retardance induced by the sample 26. The intensity information received on the second channel of the lock-in amplifier 80—as a result of the arrangement of the 0° analyzer 74—relates to the 45° or −45° component of the retardance induced by the sample. As explained below, this information is combined in an algorithm that yields an unambiguous determination of the magnitude of the overall retardance induced in beam "B1" (i.e., the normal-incidence beam) at the scanned location in the sample, as well as the orientation of the fast axis at that location in the sample.

The lock-in amplifier 80 takes as its reference signal 82 the oscillation frequency applied by the PEM controller 84 to drive the optical element 24 of the PEM 25. The lock-in amplifier 80 communicates with a digital computer 90 to provide, for a location on the sample, the values received on the two channels mentioned above, which can be designated channel 1 and channel 2. The intensity signals on the detectors in channels 1 and 2 are derived as follows:

$$I_{ch1} = 1 + \cos(4\rho)\sin^2\left[\frac{\delta_N}{2}\right]\cos\Delta - \cos^2\left[\frac{\delta_N}{2}\right] \quad \text{eqn. (1)}$$
$$\cos\Delta + \cos(2\rho)\sin\delta_N\sin\Delta$$

$$I_{ch2} = 1 + \sin(4\rho)\sin^2\left[\frac{\delta_N}{2}\right]\cos\Delta + \sin(2\rho)\sin\delta_N\sin\Delta$$

where $\Delta$ is the PEM's time-varying phase retardation; $\delta_N$ is the magnitude of the sample's retardance as respects beam "B1" (the normal-incidence beam); and p is the azimuth of the fast axis of the sample's retardance. The Mueller matrix for a linearly birefringent sample ($\delta$, $\rho$) used in the derivation has the following generalized form:

$$\begin{bmatrix} 1 & 0 & 0 & 0 \\ 0 & \cos(4\rho)\sin^2\left(\frac{\delta}{2}\right) + \cos^2\left(\frac{\delta}{2}\right) & \sin(4\rho)\sin^2\left(\frac{\delta}{2}\right) & -\sin(2\rho)\sin\delta \\ 0 & \sin(4\rho)\sin^2\left(\frac{\delta}{2}\right) & -\left(\cos(4\rho)\sin^2\left(\frac{\delta}{2}\right)\right) + \cos^2\left(\frac{\delta}{2}\right) & \cos(2\rho)\sin\delta \\ 0 & \sin(2\rho)\sin\delta & -\cos(2\rho)\sin\delta & \cos\delta \end{bmatrix}$$

In equations (1), sin Δ (Δ=Δ₀ sin ωt, where ω is the PEM's modulating frequency; $\Delta_0$ is the maximum peak retardance of the PEM) can be expanded with the Bessel functions of the first kind:

$$\sin\Delta = \sin(\Delta_0 \sin(\omega t)) = \sum_{2k+1} 2J_{2k+1}(\Delta_0)\sin((2k+1)\omega t) \quad \text{eqn. (2)}$$

where k is either "0" or a positive integer; and $J_{2k+1}$ is the (2k+1)th order of the Bessel function. Similarly, cos Δ can be expanded with the even harmonics of the Bessel functions:

$$\cos\Delta = \cos(\Delta_0 \sin(\omega t)) = J_0(\Delta_0) + \quad \text{eqn. (3)}$$

$$\sum_{2k} 2J_{2k}(\Delta_0)\cos((2k)\omega t)$$

where $J_0$ is the $0^{th}$ order of the Bessel function, and $J_{2k}$ is the (2k)th order of the Bessel function.

As seen from equations (1-3), it is preferable to determine the magnitude and angular orientation of retardance using the signal at the PEM's first harmonic.

The useful signal for measuring linear birefringence at the PEM's 2nd harmonic is modified by $\sin^2(\delta_N/2)$, a value that is much smaller than sin $\delta_N$. The 1F electronic signal on the detectors can be expressed in equation (4):

$$I_{ch1,1F} = \sin\delta\cos(2\rho)2J_1(\Delta_0)\sin(\omega t)$$

$$I_{ch2,1F} = \sin\delta\sin(2\rho)2J_1(\Delta_0)\sin(\omega t) \quad \text{eqn. (4)}$$

As noted, the 1F signal is determined using the lock-in amplifier 80 that is referenced at the PEM's first harmonic. The lock-in amplifier will exclude the contributions from all harmonics other than 1F. The output from the lock-in amplifier 80 for the two channels is:

$$I_{ch\,1}(1F) = \delta_N \cos(2\rho)2J_1(\Delta_0)\sqrt{2}$$

$$I_{ch\,2}(1F) = \delta_N \sin(2\rho)2J_1(\Delta_0)\sqrt{2} \text{eqn.} \quad (5)$$

using the approximation of sin $\delta_N \approx \delta_N$ for low-level linear birefringence; and $\sqrt{2}$ results from the fact that the lock-in amplifier measures the root-mean-square of the signal, instead of the amplitude.

All terms appearing at a frequency other than the PEM's first harmonic are neglected in obtaining equations (5). The validity of equations (5) for obtaining the 1F VAC signal is further ensured as a result of the approximation that $\sin^2(\delta_N/2) \approx 0$ when $\delta_N$ is small. This applies for low-level retardance of, for example, less than 20 nm.

In order to eliminate the effect for intensity fluctuation of the light source, or variations in transmission due to absorption, reflection losses, or scattering, the ratio of the 1F VAC signal to the VDC signal is used. (Alternatively, similar techniques can be employed, such as dynamically normalizing the DC signal to unity.) Exclusion of the cos Δ terms in equation (1) can severely affect the VDC signal in channel 1, even though it has a minimal effect on the determination of the 1F VAC signal using a high quality lock-in amplifier. The term $\cos^2(\delta_N/2)\cos\Delta$ in equation (1) is approximately equal to cos Δ for small $\delta_N$. As seen from equation (3), cos Δ depends on $J_0(\Delta_0)$, which is a "DC" term. Consequently, this DC term should be corrected as in equations (7):

$$\frac{I_{ch1}(1F)}{I_{dc}} \cdot \frac{1-J_0(\Delta_0)}{2J_1(\Delta_0)} \cdot \frac{1}{\sqrt{2}} = R_{ch1} = \delta_N \cos(2\rho) \quad \text{eqn. (7)}$$

$$\frac{I_{ch2}(1F)}{I_{dc}} \cdot \frac{1}{2J_1(\Delta_0)} \cdot \frac{1}{\sqrt{2}} = R_{ch2} = \delta_N \sin(2\rho)$$

where $R_{ch1}$ and $R_{ch2}$ are the determined quantities from the two channels.

To correct the "DC" term caused by the cos Δ term in channel 1, one sets the PEM retardation so that $J_0(\Delta_0)=0$ (when $\Delta_0=2.405$ radians, or 0.383 waves). At this PEM setting, the efficiency of the PEM for generating the 1F signal is about 90% of its maximum.

Finally, the measured magnitude $\delta_N$ (in nanometers) and angular orientation p of the in-plane retardance affecting the normal-incidence beam "B1" is expressed in equations (8):

$$\delta_N = \sqrt{(R_{ch1})^2 + (R_{ch2})^2} \text{ and } \rho = \frac{1}{2}\tan^{-1}\left[\frac{R_{ch2}}{R_{ch1}}\right] \quad \text{eqn. (8)}$$

These equations (8) are compiled in a program running on the computer 90 and used to determine the magnitude and orientation of such retardance at the selected location in the sample through which the angled-apart beams are transmitted.

Equations (8) are specifically developed for small linear birefringence. The approximation of sin $\delta_N \approx \delta_N$ used in deriving equations (8) has an error of approximately 1% for δ=20 nm when the light wavelength is at 632.8 nm. For any larger retardation, sin $\delta_N$ should be used, instead of $\delta_N$.

Notwithstanding the above-mentioned efforts to eliminate residual birefringence in the system components, such as the PEM, the presence of at least some level of residual birefringence is inevitable. In the present system, highly accurate results are obtained by correcting the results of equations (8) to account for any remaining residual birefringence in the system, which residual may be referred to as the system offset. In practice, residual birefringence in the optical element of the photoelastic modulator and in the beam-splitting mirror substrate can induce errors in the resulting measurements. Any such errors can be measured by first operating the system with no sample in place. A correction for the errors is made by subtracting the error values for each channel. In principle, this procedure will provide a method of self-calibration of the system. It is, however, prudent to compare the system measurement of a sample with the measurement obtained using other methods The value of the retardance ON induced by the in-plane birefringence of the sample is used with the simultaneously detected measure of retardance imparted into the other light beam, shown as "B2" in FIG. 1. As mentioned above, that beam "B2" is directed to be oblique to the surface of the sample 26. Beam "B2" thus exits the sample with characteristics that provide information relating to the retardance occurring along the (refracted) incident path of that beam "B2" through that sample. The information thus provided by the two angled-apart beams "B1" and "B2" is detected and processed to provide, in addition to the in-plane birefringence of the sample, the out-of-plane birefringence of the sample.

Except as discussed below, the oblique source module 14 and the oblique detection module 16 respectively match the normal source module 10 and the normal detection module 12. Thus, oblique source module 14 includes a light source 220, polarizer 222, and PEM 225 that function in the same manner as the light source 20, polarizer 22, and PEM 25 of normal source module 10. Similarly, the oblique detection module 16 includes a beam-splitting mirror 230 and detector assemblies 232, 250 that function in the same manner as the beam-splitting mirror 30 and detector assemblies 32, 50 of the normal detection module 12. In oblique detection module 16, beam "B2" is thus divided into two parts: "B2I" and "B2R" and processed in a like manner as beam parts "B1I" and B1R" in the normal detection module 12

The primary difference between the normal modules 10, 12 and the oblique modules 14, 16 is that the oblique modules are used for providing and detecting the beam "B2" that propagates through the sample 26 at an angle "A" in FIG. 1 that is oblique to the normal-incidence beam "B1." To this end, the oblique source module 14 is, in this embodiment, mounted away from the normal source module 10 and tilted by an amount that produces the angled-apart beams "B1" and "B2" propagating through the same location in the sample.

In one embodiment, the angle "A" is selected to be 30 degrees. Since the out-of-plane birefringence calculation described below involves information derived from both beams "B1" and "B2," it is preferred that the angle "A" be small enough to ensure that the sample location through which the oblique-angled beam "B2" penetrates is substantially aligned with, and not a significantly different in size than, the location through which the normal-incidence beam "B1" penetrates. Diverting the beams by an angle of 30 degrees addresses these considerations.

One of ordinary skill, following the foregoing discussion of the normal detection module 12 and associated processing of the beam "B1" received there, will understand that the detected signals applied to the lock-in amplifier 280 (FIG. 2) and processed by computer 90 will yield the measured magnitude $\delta_O$ (in nanometers) of the retardance in the oblique beam "B2." This information is employed that of the measured normal retardance $\delta_N$ to calculate, preferably simultaneously, the in-plane birefringence and the out-of-plane birefringence associated with the selected location(s) of the sample, as explained next.

As noted, $\delta_N$ represents the magnitude of the retardance, in nanometers, of the normal-incidence beam "B1" which is considered in the Z-axis. The in-plane birefringence is defined as:

$$\Delta n_{In} = n_Y - n_X = \frac{\delta_N}{d \cdot 1000} \qquad \text{eqn. (9)}$$

where $n_Y$ and $n_X$ are, respectively, the indices of refraction of the sample in the orthogonal axes, X and Y, that are perpendicular to the beam direction. The variable "d" is the sample thickness, typically measured in micrometers and, thus, multiplied here by 1000 to match the nanometer dimension of the retardance measure and thereby yield the dimensionless measure of in-plane birefringence of equation (9).

Thus, the normal retardation measurement is related to the in-plane birefringence as follows:

$$\delta_N = (n_Y - n_X) \cdot d \cdot 1000 \qquad \text{eqn. (10)}$$

Considering the situation where the value of the out-of-plane (or "vertical") birefringence in the XZ plane is sought (again, employing the Cartesian coordinate system introduced above), the out-of-plane birefringence is denoted as $\delta n_{V1} = n_Z - n_X$.

As noted above, the fast axis p of the sample is calculated as shown in equations (8). Where necessary, this information is used to ensure that the sample birefringence (fast) axis and the measurement components birefringence (fast) axis are in alignment. Then, assuming the oblique-angle beam "B2" angle "A" is φ (in this embodiment, 30 degrees), and the sample has an average index of refraction of n, the corrected incident angle inside the sample (owing to refraction) is:

$$\theta = \sin^{-1}\left[\frac{\sin\varphi}{n}\right] \qquad \text{eqn. (11)}$$

The oblique-angle retardation can then be expressed as follows:

$$\delta_O = [(n_Z \sin^2\theta + n_X \cos^2\theta) - n_Y] \cdot \frac{d \cdot 1000}{\cos\theta} \qquad \text{eqn. (12)}$$

Rearranging equations (10) and (11) yields:

$$\frac{\delta_N}{d \cdot 1000} = n_Y - n_X \qquad \text{eqn. (13)}$$

$$\frac{\delta_O}{\left(\frac{d \cdot 1000}{\cos\theta}\right)} = (n_Z \sin^2\theta + n_X \cos^2\theta) - n_Y \qquad \text{eqn. (14)}$$

which, when combined, produces:

$$\frac{\delta_O}{\left(\frac{d \cdot 1000}{\cos\theta}\right)} + \frac{\delta_N}{d \cdot 1000} = (n_Z \sin^2\theta + n_X \cos^2\theta) - n_X \qquad \text{eqn. (15)}$$

$$= (n_Z - n_X)\sin^2\theta$$

or $$\Delta n_{V1} = (n_Z - n_X) = \frac{1}{\sin^2\theta}\left\{\frac{\delta_O}{\left(\frac{d \cdot 1000}{\cos\theta}\right)} + \frac{\delta_N}{d \cdot 1000}\right\} \qquad \text{eqn. (16)}$$

which is the out-of-plane (or "vertical") birefringence of the sample in the XZ plane as calculated using the computer 90. The fast axis information can also be used to determine which refractive index component is larger in equations (10) and (12). Accordingly, the signs of the terms in equations (13)-(16) may be adjusted for the calculation.

If desired, the present system is used to determine an out-of-plane birefringence for a different vertical plane, that being in the YZ plane of the sample (that is, the plane normal to the XZ plane) as:

$$\Delta n_{V2} = (n_Z - n_Y) = \Delta n_{V1} + \Delta n_{In} \qquad \text{eqn. (17)}$$

It is contemplated that the sample 26 could be rotated in its XY plane, or a third source and detection pair could be employed for carrying out measurements of out-of-plane birefringence in more that one vertical plane as just discussed.

It is noteworthy that when the in-plane birefringence is negligible as compared to oblique birefringence, the requirement of coincidence of the X-axis and Y-axis with the birefringence axes (fast and slow axes) and the birefringence measurement system is not necessary. In such a case, the out-of-plane birefringence is:

$$\Delta n_{V1} = (n_Z - n_X) = \Delta n_{V2} = (n_Z - n_Y) \qquad \text{eqn. (18)}$$

Figure 3:
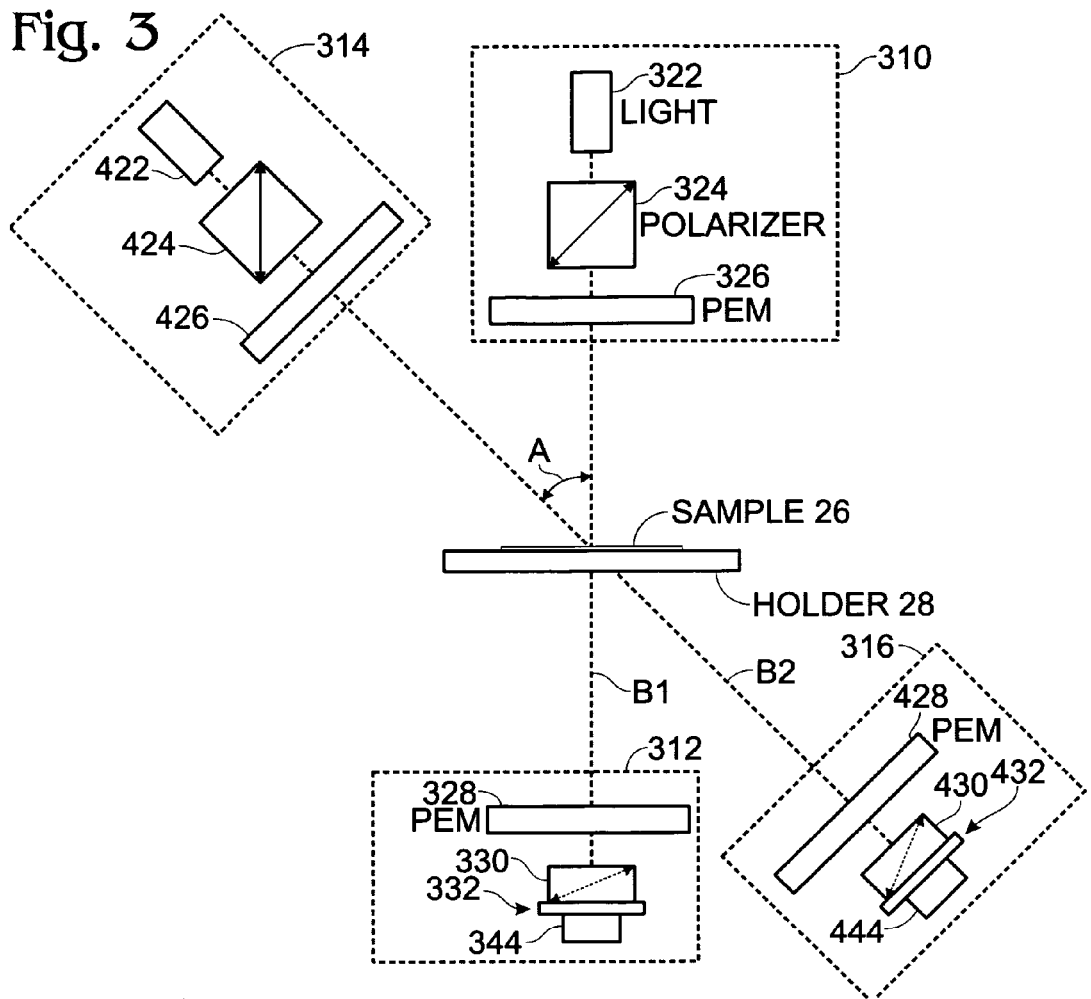
FIG. 3 is a diagram of another embodiment showing another arrangement of optical components of a system for measuring out-of-plane birefringence in accordance with the present invention.
Figure 4:
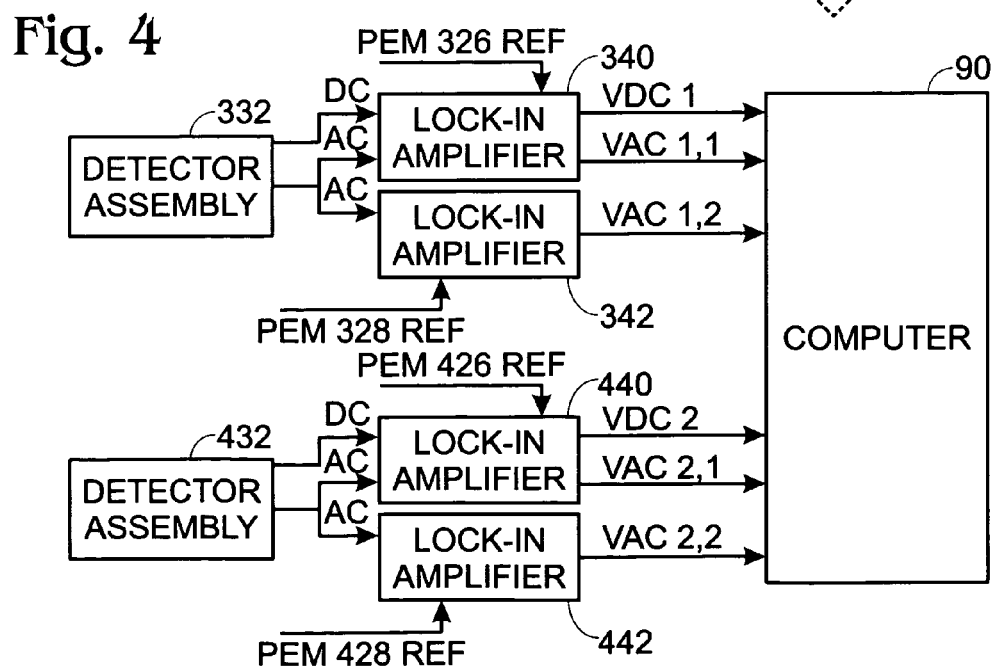
FIG. 4 is a block diagram of the signal processing components of the system depicted in FIG. 3.

FIGS. 3 and 4 respectively show a diagram of another embodiment of the present invention and a block diagram of the signal processing components of the system depicted in FIG. 3. This is a dual-PEM, single-detector embodiment that employs a different arrangement of source and detector components for determining the normal $\delta_N$ and oblique $\delta_O$ retardance measurements described above, but otherwise calculates the out-of-plane birefringence values in the manner as just discussed.

As shown in FIG. 3, the normal source module 310 includes a light source 322, a polarizer 324 oriented at +45 degrees, and a PEM 326 oriented at 0 degrees.

The normal detection module 312 includes a second PEM 328 that is set to a modulation frequency that is different from the modulation frequency of the first PEM 326. The second PEM 328 is oriented at 45 degrees. The normal detection module 312 also includes an analyzer 330 at 0 degrees and a detector assembly 332.

As in the prior embodiment, there is located between the source and detection modules the holder 28 for the transparent sample 26.

With continued reference to the normal source module 310 and detection module 312 shown in FIG. 3, source 322 is a polarized He—Ne laser at 632.8 nm wavelengths. The polarizer 324 and analyzer 330 are each a Glan-Thompson-type polarizer. A Si-photodiode detector 344 also is used in this embodiment. Both PEMs 326, 328 are bar-shaped, fused silica models having two transducers. The transducers are attached to the fused silica optical element with soft bonding material. To minimize birefringence induced in the optical element, only the transducers are mounted to the PEM housing. The two PEMs 326, 328 have nominal resonant frequencies of 50 and 55 KHz, respectively and are driven by controllers (not shown).

As shown in FIG. 4, the electronic signals generated at the detector assembly 332 contain both "AC" and "DC" signals and are processed differently. The AC signals are applied to two lock-in amplifiers 340, 342. Each lock-in amplifier, referenced at a PEM's fundamental modulation frequency (1F), demodulates the 1F signal provided by the detector assembly 332.

The DC signal is received by the lock-in amplifier 340 after the signal from the detector assembly 332 passes through an analog-to-digital converter and a low-pass electronic filter. The DC signal represents the average light intensity reaching the detector assembly 332. As discussed next, the DC and AC signals need to be recorded at different PEM retardation settings.

The theoretical analysis underlying the measurement of the birefringence properties of the sample 26 in this embodiment is also based on a Mueller matrix analysis, and is discussed next for this dual-PEM, single-detector embodiment depicted in FIGS. 3 and 4.

The Mueller matrices for each of the respective pairs of source and detection modules in FIG. 3 are shown below. The sample 26 in this optical arrangement, with a magnitude of $\delta$ (here considered in the general sense rather than in the normal/oblique sense as discussed below) and an angle of the fast axis at $\rho$, has the following form:

$$\begin{bmatrix} 1 & 0 & 0 & 0 \\ 0 & \cos(4\rho)\sin^2\left(\frac{\delta}{2}\right) + \cos^2\left(\frac{\delta}{2}\right) & \sin(4\rho)\sin^2\left(\frac{\delta}{2}\right) & -\sin(2\rho)\sin\delta \\ 0 & \sin(4\rho)\sin^2\left(\frac{\delta}{2}\right) & -\left(\cos(4\rho)\sin^2\left(\frac{\delta}{2}\right)\right) + \cos^2\left(\frac{\delta}{2}\right) & \cos(2\rho)\sin\delta \\ 0 & \sin(2\rho)\sin\delta & -\cos(2\rho)\sin\delta & \cos\delta \end{bmatrix}$$

The Mueller matrices of the two PEMs (one in the source module, the other in the detection module, with the retardation axes oriented at $\rho=0°$ and $45°$ are, respectively:

$$\begin{pmatrix} 1 & 0 & 0 & 0 \\ 0 & 1 & 0 & 0 \\ 0 & 0 & \cos(\delta 1) & \sin(\delta 1) \\ 0 & 0 & -\sin(\delta 1) & \cos(\delta 1) \end{pmatrix} \begin{pmatrix} 1 & 0 & 0 & 0 \\ 0 & \cos(\delta 2) & 0 & -\sin(\delta 2) \\ 0 & 0 & 1 & 0 \\ 0 & \sin(\delta 2) & 0 & \cos(\delta 2) \end{pmatrix}$$

where $\delta 1$ and $\delta 2$ are the time varying phase retardation of the source PEM (326 or 426) and detection PEM (328 or 428) and $\delta 1 = \delta 1_o \sin \omega_1 t$ and $\delta 2 = \delta 2_o \sin \omega_2 t$; where $\omega_1$ and $\omega_2$ are the PEMs' modulating frequencies; $\delta 1_o$ and $\delta 2_o$ are the retardation amplitudes of the two PEMs.

Using the Mueller matrices of the optical components in the set-up shown in FIG. 3, the light intensity reaching the detector (344 or 444) is obtained as follows:

$$\frac{KI_0}{2};$$

$$1 + \cos(\delta 1)\cos(\delta 2)\sin(4\rho)\sin^2\left(\frac{\delta}{2}\right) +$$
$$\sin(\delta 1)\sin(\delta 2)\cos\delta + \cos(\delta 1)\sin(\delta 2)\cos(2\rho)\sin\delta +$$
$$\sin(\delta 1)\cos(\delta 2)\sin(2\rho)\sin\delta;$$

eqn. (19)

where $I_0$ is the light intensity after the polarizer (324 or 424), and K is a constant that represents the transmission efficiency of the optical system after the polarizer.

The functions of $\sin \delta 1$ and $\cos \delta 1$ in equation 19 can be expanded with the Bessel functions of the first kind:

$$\sin\delta 1 = \sin(\delta 1_0 \sin(\omega_1 t)) \qquad \text{eqn. (20)}$$
$$= \sum_{2k+1} 2J_{2k+1}(\delta 1_0)\sin((2k+1)\omega_1 t)$$

where k is either "0" or a positive integer, and $J_{2k+1}$ is the $(2k+1)^{th}$ order of the Bessel function; and $$\cos\delta 1 = \cos(\delta 1_0 \sin(\omega_1 t)) \qquad \text{eqn. (21)}$$
$$= J_0(\delta 1_0) + \sum_{2k} 2J_{2k}(\delta 1_0)\cos((2k)\omega_1 t)$$

where $J_0$ is the $0^{th}$ order of the Bessel function, and $J_{2k}$ is the $(2k)^{th}$ order of the Bessel function.

Similar expansions can be made for $\sin \delta 2$ and $\cos \delta 2$.

Substituting the expansions of sin δ1, cos δ1, sin δ2 and cos δ2 into equation (19) and taking only up to the second order of the Bessel functions, we obtain the following terms:

$$1 + [J_0(\delta 1_0) + 2J_2(\delta 1_0)\cos(2\omega_1 t)] \cdot \quad \text{term (1)}$$
$$[J_0(\delta 2_0) + 2J_2(\delta 2_0)\cos(2\omega_2 t)]\sin(4\rho)\sin^2\left(\frac{\delta}{2}\right)$$

$$2J_1(\delta 1_0)\sin(\omega_1 t) \cdot 2J_1(\delta 2_0)\sin(\omega_2 t) \cdot \cos\delta \quad \text{term (2)}$$

$$\lfloor J_0(\delta 1_0) + 2J_2(\delta 1_0)\cos(2\omega_1 t) \rfloor \cdot \quad \text{term (3)}$$
$$\lfloor 2J_1(\delta 2_0)\sin(\omega_2 t) \rfloor \cos(2\rho)\sin\delta =$$
$$J_0(\delta 1_0) \cdot 2J_1(\delta 2_0)\sin(\omega_2 t)\cos(2\rho)\sin\delta +$$
$$2J_2(\delta 1_0)\cos(2\omega_1 t) \cdot 2J_1(\delta 2_0)\sin(\omega_2 t)\cos(2\rho)\sin\delta \cdot$$

$$\lfloor J_0(\delta 2_0) + 2J_2(\delta 2_0)\cos(2\omega_1 t) \rfloor \cdot \quad \text{term (4)}$$
$$\lfloor 2J_1(\delta 1_0)\sin(\omega_1 t) \rfloor \sin(2\rho)\sin\delta =$$
$$J_0(\delta 2_0) \cdot [2J_1(\delta 1_0)\sin(\omega_1 t)]\sin(2\rho)\sin\delta +$$
$$2J_2(\delta 2_0)\cos(2\omega_2 t) \cdot [2J_1(\delta 1_0)\sin(\omega_1 t)]\sin(2\rho)\sin\delta$$

The first parts of terms (3) and (4) can be used for determining linear retardance at low levels (below π/2 or a quarter-wave). Term (2) is useful for determining linear retardance at higher levels (up to a or a half-wave). Term (1) contains DC terms that relate to the average light intensity.

The 1F AC signals on the detector assembly (332 or 432) are determined using the lock-in amplifiers (304, 342 or 440, 442) referenced at the associated two PEMs' first harmonic (1F) frequencies. The lock-in amplifiers will effectively exclude the contributions from all other harmonics. The 1F signals measured by the lock-in amplifiers for the two PEMs are:

$$\sqrt{2} \cdot V_{1,1F} = \frac{KI_0}{2} J_0(\delta 1_0) \cdot 2J_1(\delta 2_0)\cos(2\rho)\sin\delta \quad \text{eqn. (22)}$$

$$\sqrt{2} \cdot V_{2,1F} = \frac{KI_0}{2} J_0(\delta 2_0) \cdot 2J_1(\delta 1_{01})\sin(2\rho)\sin\delta$$

where √2 results from the fact that the output of a lock-in amplifier measures the root-mean-square, not the signal amplitude. It is seen from eqn (22) that the maximum values of $J_0(\delta 1_0)2J_1((\delta 2_0)$ and $J_0(\delta 2_0)2J_1((\delta 1_0)$ will lead to optimal results for the output of the lock-in amplifiers. When the AC signals are collected, the retardation amplitudes of both PEMs are set to be 1.43 radians to optimize the AC signals.

The DC signal can be derived from term (1) to be:

$$V_{DC} = \frac{KI_0}{2}\left\{1 + J_0(\delta 1_0) \cdot J_0(\delta 2_0) \cdot \sin(4\rho)\sin^2\left(\frac{\delta}{2}\right)\right\} \quad \text{eqn. (23)}$$

where any term that varies as a function of the PEMs' modulation frequencies is omitted because they have no net contribution to the DC signal. The low-pass electronic filter mentioned above is used to eliminate such oscillations.

Within small angle approximation (sinx=x and sin²x=0 when x is small), VDC is independent of the sample's retardation and thus represents the average light intensity reaching the detector. However, when a sample with retardation above 30 nm is measured, the $V_{DC}$ as shown in equation (23) will generally be affected by the magnitude and angle of the retardance. Thus, the measured DC signal will not be a true representation of the average light intensity. In this case, the most straightforward method is to set both $J_0(\delta 1_0)$ and $J_0(\delta 2_0)$ equal to "0". The DC signal then becomes:

$$V_{DC} = \frac{KI_0}{2} \quad \text{eqn. (24)}$$

In this embodiment, the PEMs' retardation amplitude was selected as $\delta 1_0 = \delta 2_0 = 2.405$ radians (0.3828 waves) for recording the DC signal. At such PEM settings, $J_0(\delta 1_0) = J_0(\delta 2_0) = 0$. Therefore, the DC signal, independent of ρ or δ, truly indicates the average light intensity reaching the detector (244 or 444).

As seen, this method requires recording AC and DC signals at different PEM settings and thus has a slower measurement speed (about 2 seconds per data point). This method affords high accuracy measurement of linear retardance above 30 nm. When speed is critical, an alternative method can be used. If the DC signal is collected at $\delta 1_0 = \delta 2_0 = 01.43$ radians, where the AC signals are recorded, the measured retardance of a sample, using the ratio of AC to DC, will depend on the sample's angular orientation. However, the DC term is well defined in equation (23). It is, therefore, possible to reduce the angular dependence of retardance by iteration of calculation for both retardation magnitude and angle.

In order to eliminate the effect of light intensity variations due to light source fluctuations and the absorption, reflection and scattering from the sample and other optical components, the ratio of the 1F AC signal to the DC signal are used. The ratios of AC signals to the DC signal for both PEMs are represented in equation (25):

$$\frac{\sqrt{2} \cdot V_{1,1F}}{V_{DC}} = J_0(\delta 1_0) \cdot 2J_1(\delta 2_0) \sin\delta \cos(2\rho) \quad \text{eqn. (25)}$$

$$\frac{\sqrt{2} \cdot V_{2,1F}}{V_{DC}} = J_0(\delta 2_0) \cdot 2J_1(\delta 1_0) \sin\delta \sin(2\rho)$$

Defining $R_1$ and $R_2$ as corrected ratios for both PEMs yields:

$$\frac{\sqrt{2} \cdot V_{1,1F}}{J_0(\delta 1_0) \cdot 2J_1(\delta 2_0) \cdot V_{DC}} = R_1 = \sin\delta \cos(2\rho) \quad \text{eqn. (26)}$$

$$\frac{\sqrt{2} \cdot V_{2,1F}}{J_0(\delta 2_0) \cdot 2J_1(\delta 1_0) \cdot V_{DC}} = R_2 = \sin\delta \sin(2\rho)$$

Finally, the magnitude and angular orientation of the birefringence are expressed as:

$$\rho = \frac{1}{2}\tan^{-1}\left[\frac{R_2}{R_1}\right] \text{ or } \rho = \frac{1}{2}ctg^{-1}\left[\frac{R_1}{R_2}\right] \quad \text{eqn. (27)}$$

$$\delta = \arcsin\left(\sqrt{(R_1)^2 + (R_2)^2}\right)$$

where δ, represented in radians, is a scalar. When measured at a specific wavelength (i.e., 632.8 nm), it is readily converted (i.e., multiplied by 632.8/(2π)) to retardation in nanometers.

It should be emphasized that equations (27) are specifically developed for small linear birefringence due to the use of arcsine function in determining linear birefringence. Therefore, this method described here has a theoretical upper limit of $\pi/2$ or 158.2 nm when using 632.8 nm laser as the light source.

The signals at both PEMs' modulation frequencies depend on the orientation of the fast axis of the sample (see equation (24)), and the final retardation magnitudes are independent of the fast axis angles (see equation (27)). To achieve this angular independence of retardation magnitude, it is important to accurately orient all optical components in the system. Also, as with the prior described embodiment, it is prudent to correct for the existing residual linear birefringence of the instrument itself (instrument offset) even when high quality optical components are used.

The foregoing development of equations (27) was essentially offered in the general sense, and one of ordinary skill will appreciate that when the calculations provided there are applied to the information detected from normal-incidence beam "B1" (FIG. 3) there will be determined an in-plane retardance measure ON, corresponding to that same measure 8N as described above in connection with the prior-discussed embodiment.

The value of the retardance ON induced by the in-plane birefringence of the sample in the embodiment of FIG. 3 is, as before, used with the simultaneously detected measure of retardance imparted on the other, "oblique" light beam, shown as "B2" in FIG. 3. That beam "B2" is directed to be oblique to the surface of the sample 26. Beam "B2" thus exits the sample with characteristics that provide information relating to the retardance occurring along the (refracted) incident path of that beam "B2" through that sample. The information thus provided by the two angled-apart beams "B1" and "B2" is detected and processed to provide, in addition to the in-plane birefringence of the sample, the out-of-plane birefringence of the sample 26.

Except as discussed below, the oblique source module 314 and the oblique detection module 316 respectively match the normal source module 310 and the normal detection module 312. Thus, oblique source module 314 includes a light source 422, polarizer 424, and PEM 426 that function in the same manner as the light source 322, polarizer 324, and PEM 326 of normal source module 310. Similarly, the oblique detection module 316 includes another PEM 428 and detector assembly 432 that function in the same manner as the PEM 328 and detector assembly 332 of the normal detection module 312.

The primary difference between the normal modules 310, 312 and the oblique modules 314, 316 is that the oblique modules are used for providing and detecting the beam "B2" that propagates through the sample 26 at an angle "A" in FIG. 3 that is oblique to the normal-incidence beam "B1." To this end, the oblique source module 314 is mounted to produce the angled-apart beams "B1" and "B2" propagating through the same location in the sample. In this FIG. 3 embodiment, the angle "A" is selected to be 30 degrees.

In accord with the foregoing discussion of the normal detection module 312 and associated processing, one of ordinary skill will understand that the detected signals applied to the lock-in amplifiers 440, 442 (FIG. 4) and processed by computer 90 will yield the measured magnitude $\delta_O$ (in nanometers) of the retardance affecting the oblique beam "B2" (FIG. 3). This information is employed with the measure of the normal retardation $\delta_N$ to calculate, preferably simultaneously, the in-plane birefringence and out-of-plane birefringence associated with the selected location(s) of the sample, as explained above in connection with the embodiment of FIGS. 1 and 2.

Figure 5:
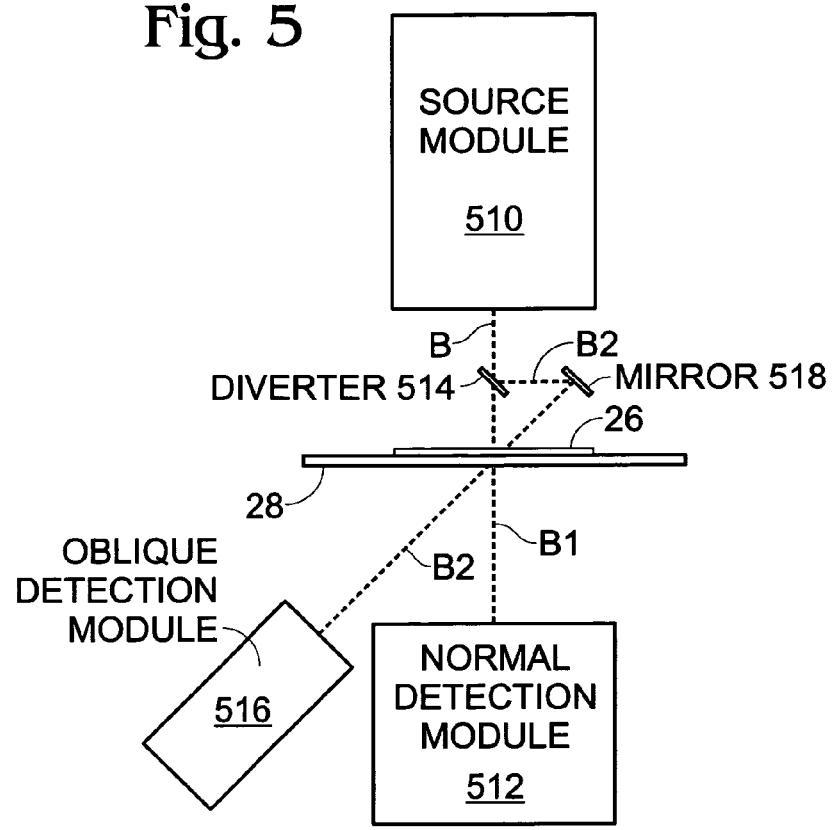
FIG. 5 is diagram of another arrangement of optical components of a system for measuring out-of-plane birefringence in accordance with the present invention.

The embodiments described above included two separate source modules and two separate corresponding detection modules. As an alternative embodiment, and as diagrammed in FIG. 5, it is contemplated that a single source module 510 may be used. In such an embodiment, the source module 510 is configured to have components (light source, PEM etc) matching those of one of the above described source modules, such as normal source module 10. The light beam "B" that emanates from the source module encounters a diverter 514 before it reaches the sample 26 on the holder 28. The diverter, which can be a partially reflective mirror, redirects some of the beam to form a diverted beam "B2" that, as shown in FIG. 5, is reflected by a mirror 518 back toward the sample 26 to intersect the beam portion "B1" that passes through the diverter 514 at a common location on the sample. Accordingly, the diverter 514 and mirror 518 are arranged to generate from the beam "B" of the single light source 510 the two, angled apart beams "B1" and "B2" for passing through the sample. As before, "B2" is preferably angled to be about 30 degrees from normal incidence.

After passing through the sample, beam "B1" (FIG. 5) is directed to detection module 512. That module 512 includes components (analyzer, detector etc) that match those described in the earlier discussed detection modules, such as detection module 12, for detecting information relating to the in-plane birefringence. Similarly, beam "B2" is directed to oblique detection module 516 after passing through the sample 26. That module 516 also includes components (analyzer, detector etc) that match those described in the earlier discussed detection modules, such as detection module 16, for detecting information relating to the oblique-angle retardation imparted into beam "B2." As before, the information collected from the normal and oblique detection modules is processed to arrive at the in-plane and out-of-plane birefringence value for the vertical plane of interest.

It is contemplated that a flip mirror could be used as the diverter 514 of the embodiment of FIG. 5. In this regard, the mirror is periodically flipped into and out of the path of beam "B" from the source module 510 thereby periodically generating the oblique beam "B2" for detection as described. Normal beam "B1" thus reaches the detection module 512, as shown, when the flip mirror is periodically out of the path of the beam "B." It will be appreciated that the frequency of the flip mirror motion can be established (as by a suitable reciprocating actuator) to be high enough for permitting substantially simultaneous detection and calculation of both the in-plane birefringence (affecting beam B1) and out-of-plane birefringence (determined with detected information from both beams B1, B2).

Figure 6:
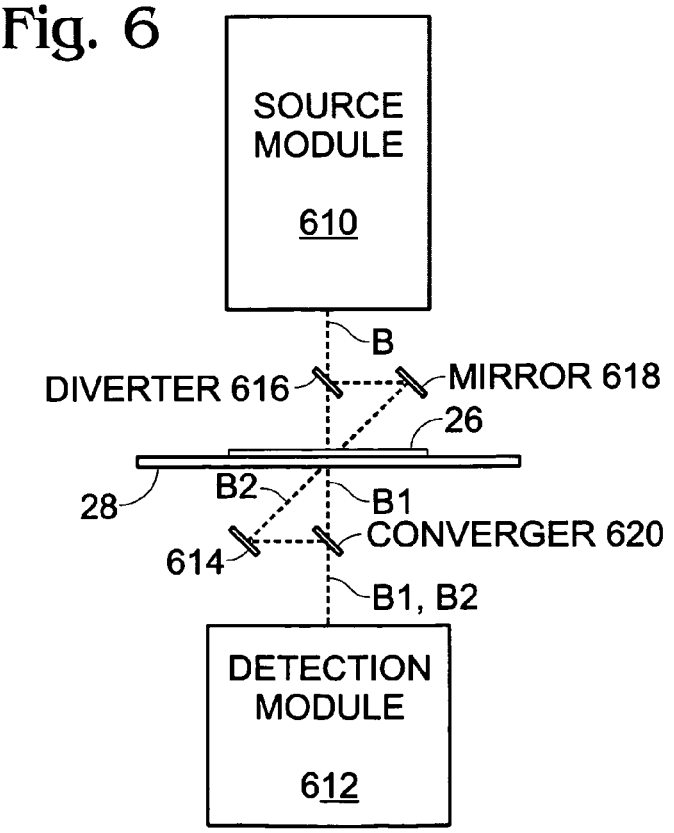
FIG. 6 is a diagram of yet another arrangement of optical components for measuring out-of-plane birefringence in accordance with the present invention.

FIG. 6 is another alternative embodiment of the present invention wherein, like that of FIG. 5, a single source module 610, diverter 616, and mirror 618 are employed for generating the two angled-apart beams "B1" and "B2" that penetrate the sample 26. In this embodiment, there is also included another mirror 614 for reflecting the oblique beam "B2" after it passes through the sample. The reflected beam impinges on a converger 620, which is located in the optical path of the normal-incident beam B1, and which path terminates in a single detection module 612. That detection module 612 has components that match earlier described detection modules, such as detection module 312 of FIG. 3.

The converger 620 permits passage of the normal-incidence beam "B1" to reach the detection module 612 while causing the other beam "B2" to converge with beam "B1" along a common axis for detection by the same detection module 612. Preferably, at least one of the diverter 616 or converger 620 will be a flip mirror that moves into and out of the path of the normal-incidence beam "B," "B1." The actuators for the flip mirror is under the control and monitoring of the computer, thereby enabling the system to readily determine which of the two, converged-path beams "B1" or "B2" is striking the single detection module at a particular time.

It is also contemplated that a sample holder could be configured to periodically tilt the sample relative to a single-source beam that travels along a single (non-diverging) path. Such tilting, as shown by the dashed line 26T in FIG. 1, would have the effect of allowing a single beam to serve as both of the above-described angled-apart beams as the sample moves into and out of the tilted position. Preferably, the holder 28 will be arranged and operated to ensure that the sample tilting occurs in a manner such that the beam penetrates the same location in the sample while information is being detected for both the normal-incidence beam (flat-oriented sample) and the oblique-incidence beam (tilted sample).

One embodiment of a tilting sample holder as just mentioned is shown diagrammatically in FIG. 7. There, a tilted sample 236 may be traversed (here in a linear, "Y," direction) across the fixed path of a light beam 221 such as the beam emanating from source module 10 as described above. The sample 236 is incrementally traversed by an X/Y stage sample holder 234 so that birefringence data can be collected over a plurality of locations across the surface of the sample. The sample holder 234 may be designed to rotate the sample to facilitate, for example, analysis of the sample's birefringence properties at a number of different angles of incidence to the light beam. For example, the holder 234 shown in FIG. 8 secures the sample 236 about aligned pivot posts 240, 241. A servomotor 235 is connected to one post or shaft 241 and operable by the computer for rotating the sample to the desired angle for analysis. In one embodiment, the servomotor is provided with an encoder that provides shaft 241 position information to the computer. The servomotor 235 can be driven to rotate the sample 236 from the angled orientation shown in solid lines in FIG. 8 to a horizontal position as shown by dashed lines 243.

In some optical applications it is desirable to use light having a very short wavelength, such as about 157 nanometers, which wavelength is often referred to as deep ultra-violet or DUV. Thus, it is important to precisely determine the characteristics of the optical elements that are used in optical systems or setups that employ DUV light. Such an element may be, for example, a calcium fluoride ($CaF_2$) lens of a scanner or stepper. Birefringence or retardance is one such characteristic of the optical element. Since the retardance of an optical element is a characteristic of both the optical material and the wavelength of the light that penetrates the material, a system for measuring retardance properties of an optical element employed in a DUV optical setup must also operate with a DUV light source and associated components in order to precisely detect and process the DUV light signals.

One problem associated with the use of DUV light in applications, such as birefringence measurement, is the absorption of DUV light by oxygen present in the system environment, and in the light beam path in particular. In this regard, the oxygen molecules (as well as other contaminants such as water vapor or trace amounts of hydrocarbons) absorb the DUV light, thus attenuating the light and reducing the signal necessary to make accurate birefringence measurements of the sample. One way of eliminating the oxygen (as well as other contaminants) in the system environment is to purge the system or beam path with nitrogen ($N_2$).

The above-described tilting sample holder embodiment of FIG. 7 may be considered as one for use in a system that requires an oxygen-purged beam path. Accordingly, there may be provided in this system a telescopic, upper purging-gas delivery tube 254 as shown schematically in FIGS. 7 and 8. Beneath the sample, there is a similar telescopic, lower purging-gas delivery tube 256.

The gas pressure supplied to the tubes 254, 256 is selected so that the purging gas exiting the tubes provides a positive pressure in the gap that resides between each tube and the sample surface, thereby preventing the entry of oxygen into the path of the DUV light beam 221.

In the drawings sequence FIGS. 7(*a*)-7(*c*), it is shown how the upper gas delivery tube 254 is retracted and the lower gas delivery tube 256 is extended as the sample 236 is traversed from left to right in the figure. From that figure, it can be appreciated that the ends of the purging gas tubes are maintained in close proximity to the surfaces of the sample, thereby ensuring that the gap that resides between the tube and the sample remains under positive pressure from the purging gas that flows from the tubes.

Figure 8:
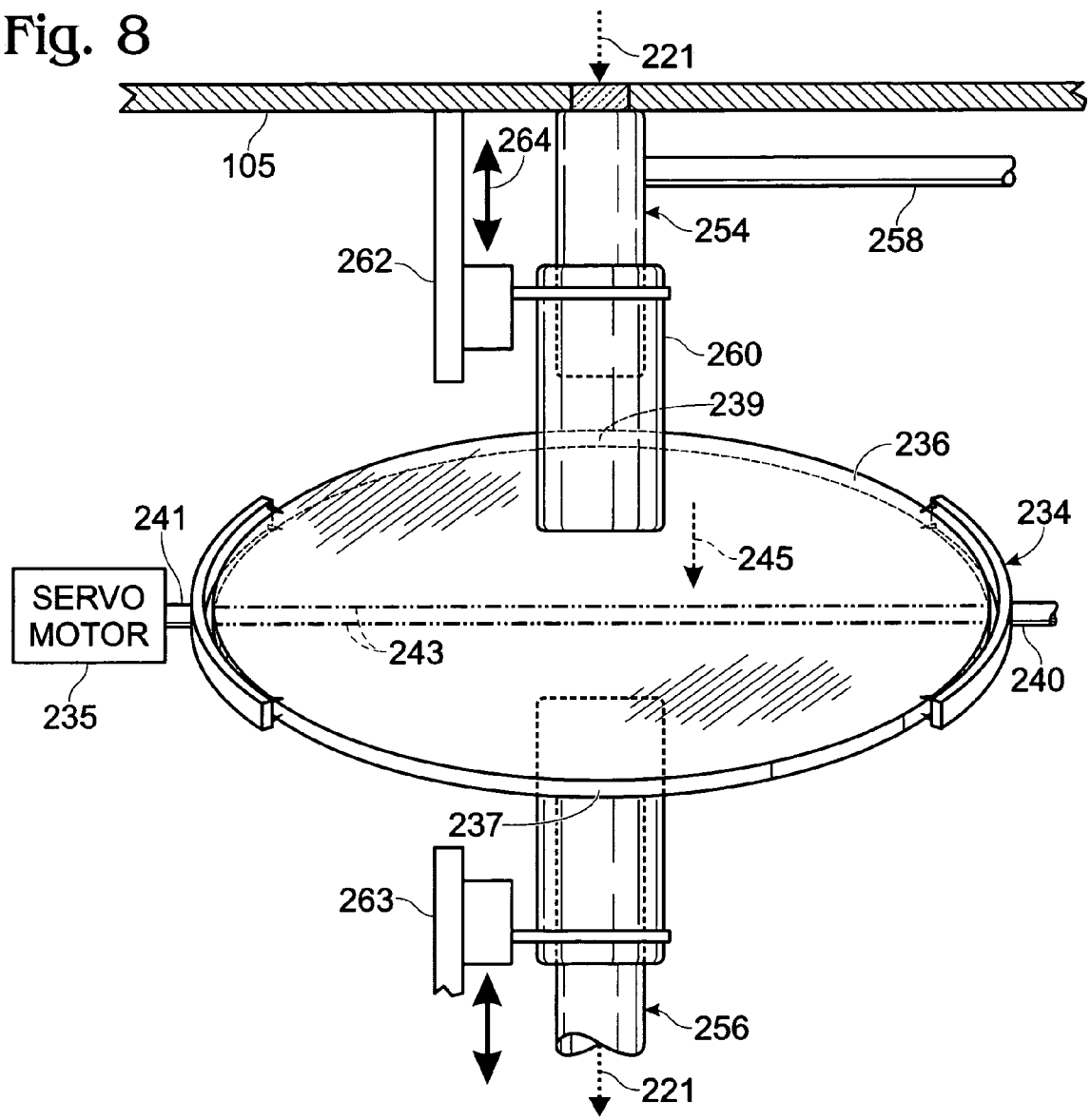
FIG. 8 is an enlarged detail diagram of the embodiment of FIG. 7 illustrating movement of purging gas delivery tubes relative to a movable, tilted sample.

With reference to FIG. 8, the adjustable purging-gas tubes 254 and 256 can be configured in any of a number of ways. In one embodiment, the telescopic upper tube 254 is mounted to protrude from a top wall 105 of a normally sealed volume within which resides the sample 236 and holder 234. A supply tube 258 delivers the pressurized purging-gas from a remote supply.

An extension part 260 of the upper tube 254 is connected to a linear actuator 262 that is mounted adjacent to the tube 254. The actuator 262, under the control of a computer, is operable to extend and retract the connected extension part 260 in the opposing directions shown by arrow 264 in FIG. 8. The lower, telescopic tube 256 is similarly extended and retracted by a computer controlled linear actuator 263.

The sample holder 234 may be constructed to hold the sample 236 in a particular angle relative to the incident light beam 221. In such an instance, the linear actuators may be controlled to maintain the ends of the tubes 256, 254 in close proximity with the respective surfaces of the sample as the sample is traversed. For example, with reference to FIG. 7, the linear actuators are controlled to incrementally retract the upper tube 254 and extend the lower tube 256 as the sample is traversed from left to right in that figure.

One of ordinary skill will understand that one effect of tilting the sample from horizontal is to alter the path of the light beam propagating through the sample. For example, as illustrated in FIG. 9, a light beam "impinging" path 400 that normally (that is, at zero incidence angle) impinges upon an optical element or sample 402 (here a horizontally oriented sample 402 is shown in solid lines), will emanate from that sample along an "emanating" path 404 that is axially aligned with the impinging beam path 400. The beam thus follows this path 404 to the next optical element 406 in the setup.

In instances where the sample 402 is tilted by an angle $\theta$ (as shown in dashed lines in FIG. 9), the emanating beam path 404 will be displaced by a distance "D" from the impinging path. The magnitude of this displacement "D" is a function of sample's refractive index, thickness, and tilt angle $\theta$.

In some birefringence measurement systems it is desirable to measure birefringence at a high spatial resolution across the sample. Thus, relatively small apertures are employed in the setup to establish a small-diameter beam size and correspondingly high resolution. For example, a small-diameter aperture may be placed adjacent to a detector that receives the light beam traveling along the emanating path 404 from the sample.

In such a system, and where one employs a mechanism for tilting the sample and imparting the above-mentioned displacement "D" in the emanating beam path 404, it is important that the optical elements in the emanating path 404 are configured and arranged to receive the displaced emanating beam (or, at least, a usable part of that beam) for further signal processing as described above. One way of accomplishing this is to locate any beam-diameter-sizing apertures in the impinging beam path 400, thereby to ensure such apertures are unaffected by displacement of the beam.

Also, since the maximum amount of deflection "D" may be predetermined, the optical setup can be provided with apertures in the emanating beam path that are sufficiently sized to capture a usable part of the displaced emanating beam, irrespective of the amount of the displacement. In this regard, a slightly diverging source beam is preferred. While the usable part of the captured beam may have significantly lower intensity as compared to the entire beam, an accurate measurement can still be achieved by accounting for this lower intensity. For example, as noted above, the ratio of the detected AC (modulated) signal to the DC (average) signal is used in determining retardance in conditions where the detected light intensity may fluctuate.

When the sample is tilted about a single axis (as discussed above in connection with FIGS. 7 and 8), the displacement of the emanating beam path 404 will be in a substantially linear, single direction or axis. With this single-direction displacement in mind, a rectangular-shaped aperture may be employed adjacent to a detector (that is, across the working surface of the detector) and arranged so that the long side of the aperture is parallel to the axis along which the beam is displaced (the "Y" axis in FIG. 7). Such an aperture will be useful for limiting the amount of undesirable, non-parallel light rays from reaching the detector.

In the embodiment discussed above with respect to FIG. 3, a PEM was one of the optical elements through which a light beam emanating from a sample is directed for additional phase modulation. Thus, element 406 in FIG. 9 will be considered to be a PEM for the purposes of the following discussion.

The retardation amplitude introduced into the emanating beam 404 by the oscillating PEM 406 may vary somewhat depending upon the amount of displacement "D" of the emanating beam from a given location on the optical element of the PEM. For example, when the PEM's optical element (shown at 408 in FIG. 9) is mounted between and driven by two transducers 410, the retardation magnitude imparted to a beam passing through the center of the element 408 will be somewhat larger than the retardation imparted to a beam that is displaced from center by an amount "D."

As noted, the amount of deflection "D" is readily determined, and where the amount of change in retardation imparted by the PEM 406 is considered significant (an "error" amount), one can determine this error and employ it in the appropriate equations noted above. For example, for a PEM optical element 408 of length "L" (between the transducers 410) and a beam displacement "D," the retardation error amount will be a function of the ratio 2D/L.

It is also contemplated that the error be empirically determined for various increments of "D" and stored in a look-up table in firmware associated with the overall signal processing. Information relating to the sample holder's angular position (derived form the servomotor and encoder mechanisms mentioned above) can be used by the controlling computer to determine a current displacement "D" that in turn is used in consulting the look-up table to arrive at the above mentioned retardation error associated with the current displacement.

While the present invention has been described in terms of preferred embodiments, it will be appreciated by one of ordinary skill in the art that modifications may be made without departing from the teachings and spirit of the foregoing.

The invention claimed is:

1. A method of determining out-of-plane birefringence of a transparent sample, comprising the steps of:
    passing two angled-apart light beams through a location in the sample;
    detecting characteristics of the light beams that have passed through the location; and
    using the detected characteristics for calculating out-of-plane birefringence of the sample.

2. The method of claim 1 including the step of angling the beams to be about 30 degrees apart.

3. The method of claim 1 wherein the passing step includes providing two separate sources of light for generating the light beams.

4. The method of claim 1 including the step of phase modulating each light beam before it passes through the sample.

5. The method of claim 4 including the step of using a photoelastic modulator for the phase modulation.

6. The method of claim 4 including the step of phase modulating each light beam after each light beam passes through the sample.

7. The method of claim 6 including the step of using a photoelastic modulator for the phase modulation of each light beam after each light beam passes through the sample.

8. The method of claim 1 wherein the sample has an outer surface and including the step of directing one of the angled-apart light beams to be at a normal incidence angle to the outer surface.

9. The method of claim 1 wherein the detecting step includes separating each of the light beams into two parts after each beam is through the sample; and directing each part of the two beams to a separate a detector.

10. The method of claim 1 wherein the passing step includes the steps of:
    providing a single source of light for generating a first light beam; and
    diverging the first light beam to provide the two angled-apart light beams.

11. The method of claim 10 wherein the diverging step includes continuously diverging at least part of the first light beam to provide the two angled-apart light beams.

12. The method of claim 10 wherein the diverging step includes periodically diverging the first light beam to provide the two angled-apart light beams.

13. The method of claim 10 including the step of providing detectors for receiving each of the angled-apart light beams after each such angled-apart light beam passes through the sample.

14. The method of claim 10 including the step of converging the two angled-apart light beams after those beams pass through the sample.

15. The method of claim 14 wherein the converging step includes directing the two angled-apart light beams along a common axis after those beams pass through the sample.

16. The method of claim 15 including the step of using a single detector for detecting characteristics of the light beams that pass through the sample.

17. The method of claim 11 including the step of using two detectors for simultaneously detecting characteristics of the light beams that pass through the sample.

18. The method of claim 1 including the steps of periodically moving the sample so that the angled-apart light beams are directed through a plurality of locations on the sample, and calculating out-of-plane birefringence of the sample at the plurality of locations.

19. The method of claim 1 including the step of orienting the angled-apart light beams to be in a first plane relative to a predetermined axis in the sample.

20. The method of claim 19 including the step of periodically changing the position of the beams thereby to change the position of the first plane relative to the sample axis.

21. The method of claim 1 wherein the passing step includes tilting the sample.

22. The method of claim 1 including the step of rotating the sample and re-calculating the out-of-plane birefringence at the location in the sample.

23. The method of claim 1 including the step of calculating the in-plane birefringence at the location in the sample in addition to calculating the out-of-plane birefringence at the location in the sample.

24. The method of claim 1 including the step of calculating the in-plane birefringence at the location in the sample simultaneously with calculating the out-of-plane birefringence at the location.

25. The method of claim 1 including the step of using the detected characteristics of one beam for establishing a fast axis of the in-plane birefringence of the sample.

26. An arrangement of optical system components for measuring out-of-plane birefringence of a transparent sample, comprising:

at least one source of light;

diverting means associated with the light source for passing two angled-apart light beams through a common location in the sample; and detection means for detecting characteristics of the light beams that have passed through the location for use in calculating the out-of-plane birefringence of the sample.

27. The arrangement of claim 26 including converging means directing the two angled-apart light beams along a common axis after each light beam passes through the sample.

28. The arrangement of claim 26 including processing means for substantially simultaneously processing the in-plane and out-of-plane birefringence of the location of the sample.

29. A method of measuring out-of-plane birefringence of a transparent sample that has an outer surface, comprising the steps of:

determining at a location in the sample the in-plane birefringence;

determining at the location in the sample the retardance affecting light propagating through the sample at an angle that is oblique to the outer surface; and calculating the out-of-plane birefringence as a function of the determined in-plane birefringence and the determined retardance.

30. The method of claim 29 including the step of substantially simultaneously determining the in-plane birefringence and out-of-plane birefringence.

* * * * *